(12) United States Patent
McCarthy et al.

(10) Patent No.: US 7,175,982 B1
(45) Date of Patent: Feb. 13, 2007

(54) METHOD FOR THE CHARACTERIZATION OF NUCLEIC ACID MOLECULES INVOLVING GENERATION OF EXTENDIBLE UPSTREAM DNA FRAGMENTS RESULTING FROM THE CLEAVAGE OF NUCLEIC ACID AT AN ABASIC SITE

(75) Inventors: Thomas Valentine McCarthy, Cork (IE); Patrick Martin Vaughan, Cork (IE)

(73) Assignees: Enterprise Ireland (T/A BioResearch Ireland), Dublin (IE); University College Cork Natl. University of Ireland, Cork (IE)

( * ) Notice: Subject to any disclaimer, the term of this patent is extended or adjusted under 35 U.S.C. 154(b) by 0 days.

(21) Appl. No.: 09/673,739

(22) PCT Filed: Apr. 22, 1998

(86) PCT No.: PCT/IE98/00030

§ 371 (c)(1),
(2), (4) Date: Oct. 20, 2000

(87) PCT Pub. No.: WO99/54501

PCT Pub. Date: Oct. 28, 1999

(51) Int. Cl.
*C12Q 1/68* (2006.01)
*C12P 19/34* (2006.01)
(52) U.S. Cl. ................... 435/6; 435/91.2; 435/91.52
(58) Field of Classification Search ............... 435/6, 435/91.2, 91.52
See application file for complete search history.

(56) References Cited

U.S. PATENT DOCUMENTS 5,656,430 A * 8/1997 Chirikjian et al. ............. 435/6

5,952,176 A * 9/1999 McCarthy et al. ............. 435/6

FOREIGN PATENT DOCUMENTS

| WO | 96 30545 A | 10/1996 |
|---|---|---|
| WO | 97 03210 A | 1/1997 |
| WO | 97 12061 A | 4/1997 |

OTHER PUBLICATIONS

Dianov et al. Generation of single-nucleotide repair patches following excision of uracil residues from DNA, 1992, vol. 12(4), pp. 1605-1612.*
Landegren, Trends in Genetics, 1993, vol. 9(6).*
Vaughan, P. et al. "A novel process for mutation detection using uracil DNA-glycosylase", Nucleic Acids Research, vol. 26, No. 12, Feb. 1998, pp. 810-815.
McGrath, A. et al. "A DNA glycolase-based fingerprint for accurate identification of amplified DNA products and its application in the Accurate diagnosis of infectious organisms", Analytical Biochemistry, vol. 259, No. 2, Jun. 1998, pp. 288-292.

* cited by examiner

Primary Examiner—Kenneth R. Horlick
Assistant Examiner—Joyce Tung
(74) Attorney, Agent, or Firm—Birch, Stewart, Kolasch & Birch, LLP

(57) ABSTRACT

The present invention is drawn to a method for characterising nucleic acid molecules, which comprises the steps of: i) introducing a modified base which is a substrate for a DNA glycosylase into a DNA molecule; ii) excising the modified base with the DNA glycosylase to generate an abasic site; iii) cleaving the DNA at the abasic site to generate and release an extendible upstream DNA fragment having a 3' hydroxyl terminus; and iv) incubating the released extendible upstream DNA fragment in the presence of an enzyme allowing for extension thereof and an additional template nucleic acid and analysing resultant fragment(s).

22 Claims, 7 Drawing Sheets

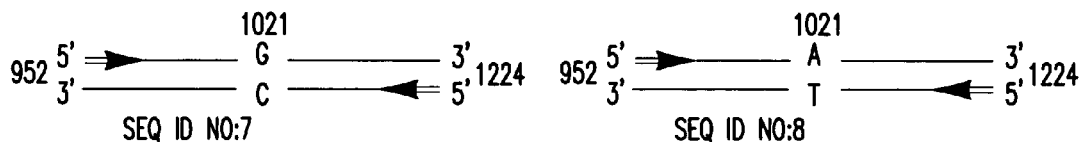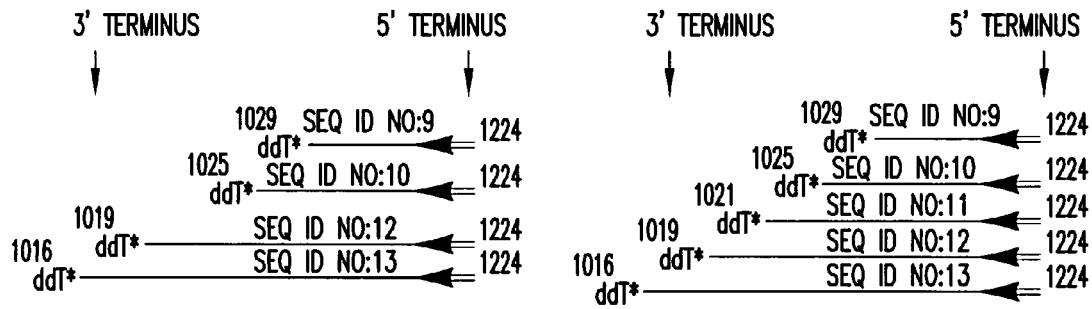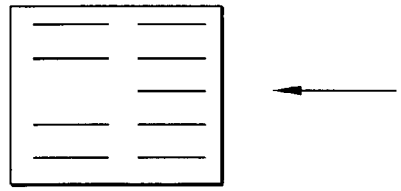
FIG.3

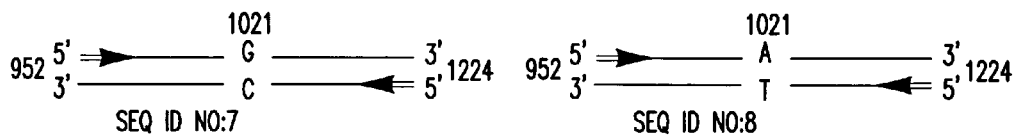
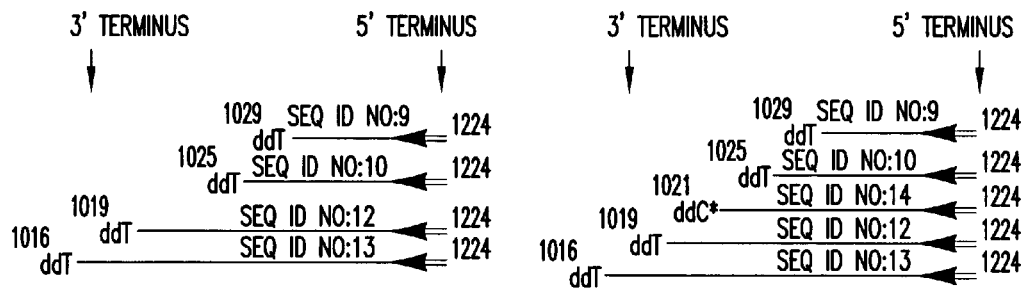
FIG.4

```
          UPPER PRIMER         MUTATION SITE
6390                           A          SEQ ID NO:15                    6443
5' [AACTTGTGGTAGTTGGAGCT]GGTGGCGTAGGCAAGAGTGCCTTGACGATACAGC 3'
3'  TTGAACACCATCAACCTCGACCACCGC[ATCCGTTCTCACGGAACTGCTATGTCG] 5'
                           T                         LOWER PRIMER
```

AMPLIFICATION OF TARGET NUCLEIC ACID IN THE PRESENCE OF dGTP, dATP, dUTP, AND dCTP.

```
         SEQ ID NO:16               AMPLIFIED MUTANT ALLELE
5' AACTTGTGGTAGTTGGAGCTGGUGGCGUAGGCAAGAGUGCCUUGACGAUACAGC 3'
3' UUGAACACCAUCAACCUCGACUACCGCATCCGTTCTCACGGAACTGCTATGTCG 5'
         SEQ ID NO:17

SEQ ID NO:18               AMPLIFIED MUTANT ALLELE
5' AACTTGTGGTAGTTGGAGCTGAUGGCGUAGGCAAGAGUGCCUUGACGAUACAGC 3'
3' UUGAACACCAUCAACCUCGACCACCGCATCCGTTCTCACGGAACTGCTATGTCG 5'
         SEQ ID NO:19
```

- TREATMENT WITH EXONUCLEASE I AND SHRIMP ALKALINE PHOSPHATASE.
- TREATMENT WITH UDG.
- TREATMENT WITH ENDO IV.

```
       SEQ ID NO:20           NORMAL UPSTREAM FRAGMENT
    3' CGACCACCGCATCCGTTCTCACGGAACTGCTATGTCG 5'

SEQ ID NO:21           MUTANT UPSTREAM FRAGMENT
    3'      ACCGCATCCGTTCTCACGGAACTGCTATGTCG 5'
```

REVERSE PRIMER SEQ ID NO:23
5' GCTGTAAACGACGGCCAGTTTCAT 3'         SYNTHETIC TEMPLATE NO.1   SEQ ID NO:22
5' GCTGTAAACGACGGCCAGTTTCATGCAGGGCTGGAGTCGTAGGCAAGAGTGCCTTGACGATACAGC 3'
                                          x x
                              3' CGACCACCGCATCCGTTCTCACGGAACTGCTATGTCG 5'
                                          NORMAL UPSTREAM FRAGMENT
PCR AMPLIFICATION IN PRESENCE OF α³²PdCTP                SEQ ID NO:20
FOLLOWED BY DENATURING PAGE
                                                  SEQ ID NO:24
3' CGACATTTGCTGCCGGTCAAAGTACGTCCCGACCACCGCATCCGTTCTCACGGAACTGCTATGTCG 5'
    *  *    *  **   *     *  **                66MER

---

B

REVERSE PRIMER SEQ ID NO:23
5' GCTGTAAACGACGGCCAGTTTCAT 3'         SYNTHETIC TEMPLATE NO.2   SEQ ID NO:25
5' GCTGTAAACGACGGCCAGTTTCATGCAGGATCCATGGCGTAGGCAAGAGTGCCTTGACGATACCGC 3'
                                        xxxxx
                              3' CGACCACCGCATCCGTTCTCACGGAACTGCTATGTCG 5'
                                          NORMAL UPSTREAM FRAGMENT
PCR AMPLIFICATION IN PRESENCE OF α³²PdCTP                SEQ ID NO:20
FOLLOWED BY DENATURING PAGE
                                                  X

---

C

REVERSE PRIMER SEQ ID NO:23
5' GCTGTAAACGACGGCCAGTTTCAT 3'         SYNTHETIC TEMPLATE NO.2   SEQ ID NO:25
5' GCTGTAAACGACGGCCAGTTTCATGCAGGATCCATGGCGTAGGCAAGAGTGCCTTGACGATACAGC 3'

3' ACCGCATCCGTTCTCACGGAACTGCTATGTCG 5'
                                          MUTANT UPSTREAM FRAGMENT
PCR AMPLIFICATION IN PRESENCE OF α³²PdCTP                SEQ ID NO:21
FOLLOWED BY DENATURING PAGE
                                                  SEQ ID NO:26
3' CGACATTTGCTGCCGGTCAAAGTACGTCCTAGGTACCGCATCCGTTCTCACGGAACTGCTATGTCG 5'
    *  *    *  **   *     *  **                66MER

---

D

REVERSE PRIMER SEQ ID NO:23
5' GCTGTAAACGACGGCCAGTTTCAT 3'         SYNTHETIC TEMPLATE NO.1   SEQ ID NO:22
5' GCTGTAAACGACGGCCAGTTTCATGCAGGGCTGGAGTCGTAGGCAAGAGTGCCTTGACGATACAGC 3'
                                          x x
                                   3' ACCGCATCCGTTCTCACGGAACTGCTATGTCG 5'
                                          MUTANT UPSTREAM FRAGMENT
PCR AMPLIFICATION IN PRESENCE OF α³²PdCTP                SEQ ID NO:21
FOLLOWED BY DENATURING PAGE
                                          MISMATCHES DENOTED BY X
                                  X       ³²P LABEL DENOTED BY *

FIG.6

SEQUENCE LISTING

```
<160> NUMBER OF SEQ ID NOS:   32

<210> SEQ ID NO 1
<211> LENGTH: 93
<212> TYPE: DNA
<213> ORGANISM: Homo sapiens

<400> SEQUENCE: 1
tccaaggaga agctggatgt ggcccccaag cgggatgtgg agggcatggg cccccctgag      60
atcaagtacg gggagtcact gtgcttcgtg cag                                   93

<210> SEQ ID NO 2
<211> LENGTH: 93
<212> TYPE: DNA
<213> ORGANISM: Artificial
<220> FEATURE:
<223> OTHER INFORMATION: DNA generated by PCR amplification and derived
```

```
from Homo sapiens.

<400> SEQUENCE: 2
tccaaggaga agctggatgt ggcccccaag cgggaugugg agggcauggg cccccugag      60 aucaaguacg gggagucacu gugcuucgug cag                                   93

<210> SEQ ID NO 3
<211> LENGTH: 93
<212> TYPE: DNA
<213> ORGANISM: Artificial
<220> FEATURE:
<223> OTHER INFORMATION: DNA generated by PCR amplification and derived
      from Homo sapiens.

<400> SEQUENCE: 3
ctgcacgaag cacagtgact ccccguacuu gaucucaggg gggcccaugc ccuccacauc      60
ccgcuugggg gccacaucca gcuucuccuu gga                                   93

<210> SEQ ID NO 4
<211> LENGTH: 25
<212> TYPE: DNA
<213> ORGANISM: Artificial
<220> FEATURE:
<223> OTHER INFORMATION: DNA derived from Homo sapiens and generated by
      glycosylase mediated cleavage and has a 3' phosphate group

<400> SEQUENCE: 4
ctgcacgaag cacagtgact ccccg                                            25

<210> SEQ ID NO 5
<211> LENGTH: 25
<212> TYPE: DNA
<213> ORGANISM: Artificial
<220> FEATURE:
<223> OTHER INFORMATION: DNA derived from Homo sapiens and generated by
      glycosylase mediated cleavage and has a 3' hydroxyl group

<400> SEQUENCE: 5
ctgcacgaag cacagtgact ccccg                                            25

<210> SEQ ID NO 6
<211> LENGTH: 93
<212> TYPE: DNA
<213> ORGANISM: Artificial
<220> FEATURE:
<223> OTHER INFORMATION: DNA derived from Homo sapiens and generated by
      glycosylase mediated cleavage followed by extension of upstream
      fragment

<400> SEQUENCE: 6
ctgcacgaag cacagtgact ccccgtactt gatctcaggg gggcccatgc cctccacatc      60
ccgcttgggg gccacatcca gcttctcctt gga                                   93

<210> SEQ ID NO 7
<211> LENGTH: 273
<212> TYPE: DNA
<213> ORGANISM: Homo sapiens

<400> SEQUENCE: 7
tccaaggaga agctggatgt ggcccccaag cgggatgtgg agggcatggg cccccctgag      60
atcaagtacg gggagtcact gtgcttcgtg cagcatgtgg cctcaggact gtggctcacc    120
tatgccgctc agaccccaa ggccctgcgg ctcggcgtgc tcaagaagaa ggccatgctg    180
```

```
caccaggagg gccacatgga cgacgcactg tcgctgaccc gctgccagca ggaggagtcc    240
caggccgccc gcatgatcca cagcaccaat ggc                                 273
```

<210> SEQ ID NO 8
<211> LENGTH: 273
<212> TYPE: DNA
<213> ORGANISM: Homo sapiens

<400> SEQUENCE: 8

```
tccaaggaga agctggatgt ggcccccaag cgggatgtgg agggcatggg ccccccctgag    60 atcaagtaca gggagtcact gtgcttcgtg cagcatgtgg cctcaggact gtggctcacc   120
tatgccgctc cagaccccaa ggccctgcgg ctcggcgtgc tcaagaagaa ggccatgctg   180
caccaggagg gccacatgga cgacgcactg tcgctgaccc gctgccagca ggaggagtcc   240
caggccgccc gcatgatcca cagcaccaat ggc                                 273
```

<210> SEQ ID NO 9
<211> LENGTH: 196
<212> TYPE: DNA
<213> ORGANISM: Artificial
<220> FEATURE:
<223> OTHER INFORMATION: DNA derived from Homo sapiens and generated by
      glycosylase mediated cleavage and upstream fragment extension, and
      has a 3' hydrogen atom
<221> NAME/KEY: modified_base
<222> LOCATION: (196)..(196)
<223> OTHER INFORMATION: mod_base = Dideoxy T

<400> SEQUENCE: 9

```
gccattggtg ctgtggatca tgcgggcggc ctgggactcc tcctgctggc agcgggtcag    60
cgacagtgcg tcgtccatgt ggccctcctg gtgcagcatg gccttcttct tgagcacgcc   120
gagccgcagg gccttggggt ctggagcggc ataggtgagc cacagtcctg aggccacatg   180
ctgcacgaag cacagt                                                    196
```

<210> SEQ ID NO 10
<211> LENGTH: 200
<212> TYPE: DNA
<213> ORGANISM: Artificial
<220> FEATURE:
<223> OTHER INFORMATION: DNA derived from Homo sapiens and generated by
      glycosylase mediated cleavage followed by upstream fragment
      extension, and has a 3' hydrogen atom
<221> NAME/KEY: modified_base
<222> LOCATION: (200)..(200)
<223> OTHER INFORMATION: mod_base = dideoxy T

<400> SEQUENCE: 10

```
gccattggtg ctgtggatca tgcgggcggc ctgggactcc tcctgctggc agcgggtcag    60
cgacagtgcg tcgtccatgt ggccctcctg gtgcagcatg gccttcttct tgagcacgcc   120
gagccgcagg gccttggggt ctggagcggc ataggtgagc cacagtcctg aggccacatg   180
ctgcacgaag cacagtgact                                                200
```

<210> SEQ ID NO 11
<211> LENGTH: 204
<212> TYPE: DNA
<213> ORGANISM: Artificial
<220> FEATURE:
<223> OTHER INFORMATION: DNA derived from Homo sapiens and generated by
      glycosylase mediated cleavage followed by upstream fragment
      extension, and has a 3' hydrogen atom
<221> NAME/KEY: modified_base
<222> LOCATION: (204)..(204)

<223> OTHER INFORMATION: mod_base = Dideoxy T

<400> SEQUENCE: 11

```
gccattggtg ctgtggatca tgcgggcggc ctgggactcc tcctgctggc agcgggtcag    60
cgacagtgcg tcgtccatgt ggccctcctg gtgcagcatg gccttcttct tgagcacgcc   120
gagccgcagg gccttggggt ctggagcggc ataggtgagc cacagtcctg aggccacatg   180
ctgcacgaag cacagtgact ccct                                          204
```

<210> SEQ ID NO 12
<211> LENGTH: 206
<212> TYPE: DNA
<213> ORGANISM: Artificial
<220> FEATURE:
<223> OTHER INFORMATION: DNA derived from Homo sapiens and generated by glycosylase mediated cleavage followed by upstream fragment extension, and has a 3' hydrogen atom
<221> NAME/KEY: modified_base
<222> LOCATION: (206)..(206)
<223> OTHER INFORMATION: mod_base = Dideoxy T

<400> SEQUENCE: 12

```
gccattggtg ctgtggatca tgcgggcggc ctgggactcc tcctgctggc agcgggtcag    60
cgacagtgcg tcgtccatgt ggccctcctg gtgcagcatg gccttcttct tgagcacgcc   120
gagccgcagg gccttggggt ctggagcggc ataggtgagc cacagtcctg aggccacatg   180
ctgcacgaag cacagtgact ccccgt                                        206
```

<210> SEQ ID NO 13
<211> LENGTH: 209
<212> TYPE: DNA
<213> ORGANISM: Artificial
<220> FEATURE:
<223> OTHER INFORMATION: DNA derived from Homo sapiens and generated by glycosylase mediated cleavage followed by upstream fragment extension, and has a 3' hydrogen atom
<221> NAME/KEY: modified_base
<222> LOCATION: (209)..(209)
<223> OTHER INFORMATION: mod_base = Dideoxy T

<400> SEQUENCE: 13

```
gccattggtg ctgtggatca tgcgggcggc ctgggactcc tcctgctggc agcgggtcag    60
cgacagtgcg tcgtccatgt ggccctcctg gtgcagcatg gccttcttct tgagcacgcc   120
gagccgcagg gccttggggt ctggagcggc ataggtgagc cacagtcctg aggccacatg   180
ctgcacgaag cacagtgact ccccgtact                                     209
```

<210> SEQ ID NO 14
<211> LENGTH: 204
<212> TYPE: DNA
<213> ORGANISM: Artificial
<220> FEATURE:
<223> OTHER INFORMATION: DNA derived from Homo sapiens and generated by glycosylase mediated cleavage followed by upstream fragment extension, and has a 3' hydrogen atom
<221> NAME/KEY: modified_base
<222> LOCATION: (204)..(204)
<223> OTHER INFORMATION: mod_base = Dideoxy C

<400> SEQUENCE: 14

```
gccattggtg ctgtggatca tgcgggcggc ctgggactcc tcctgctggc agcgggtcag    60
cgacagtgcg tcgtccatgt ggccctcctg gtgcagcatg gccttcttct tgagcacgcc   120
gagccgcagg gccttggggt ctggagcggc ataggtgagc cacagtcctg aggccacatg   180
```

```
ctgcacgaag cacagtgact cccc                                          204
```

```
<210> SEQ ID NO 15
<211> LENGTH: 54
<212> TYPE: DNA
<213> ORGANISM: Homo sapiens

<400> SEQUENCE: 15
aacttgtggt agttggagct ggtggcgtag gcaagagtgc cttgacgata cagc         54

<210> SEQ ID NO 16
<211> LENGTH: 54
<212> TYPE: DNA
<213> ORGANISM: Homo sapiens
<220> FEATURE:
<221> NAME/KEY: misc_feature
<222> LOCATION: (1)..(54)
<223> OTHER INFORMATION: Generated by PCR amplification of genomic DNA

<400> SEQUENCE: 16
aacttgtggt agttggagct gguggcguag gcaagagugc cuugacgaua cagc         54

<210> SEQ ID NO 17
<211> LENGTH: 54
<212> TYPE: DNA
<213> ORGANISM: Homo sapiens
<220> FEATURE:
<221> NAME/KEY: misc_feature
<222> LOCATION: (1)..(54)
<223> OTHER INFORMATION: Generated by PCR amplification of genomic DNA

<400> SEQUENCE: 17
gctgtatcgt caaggcactc ttgcctacgc caccagcucc aacuaccaca aguu         54

<210> SEQ ID NO 18
<211> LENGTH: 54
<212> TYPE: DNA
<213> ORGANISM: Homo sapiens
<220> FEATURE:
<221> NAME/KEY: misc_feature
<222> LOCATION: (1)..(54)
<223> OTHER INFORMATION: Generated by PCR amplification of genomic DNA

<400> SEQUENCE: 18
aacttgtggt agttggagct gauggcguag gcaagagugc cuugacgaua cagc         54

<210> SEQ ID NO 19
<211> LENGTH: 54
<212> TYPE: DNA
<213> ORGANISM: Homo sapiens
<220> FEATURE:
<221> NAME/KEY: misc_feature
<222> LOCATION: (1)..(54)
<223> OTHER INFORMATION: Generated by PCR amplification of genomic DNA

<400> SEQUENCE: 19
gctgtatcgt caaggcactc ttgcctacgc caucagcucc aacuaccaca aguu         54

<210> SEQ ID NO 20
<211> LENGTH: 37
<212> TYPE: DNA
<213> ORGANISM: Homo sapiens
<220> FEATURE:
<221> NAME/KEY: misc_feature
<222> LOCATION: (1)..(37)
<223> OTHER INFORMATION: generated by glycosylase mediated cleavage of
      PCR amplified DNA
```

```
<400> SEQUENCE: 20
gctgtatcgt caaggcactc ttgcctacgc caccagc                              37

<210> SEQ ID NO 21
<211> LENGTH: 32
<212> TYPE: DNA
<213> ORGANISM: Homo sapiens
<220> FEATURE:
<221> NAME/KEY: misc_feature
<222> LOCATION: (1)..(32)
<223> OTHER INFORMATION: generated by glycosylase mediated cleavage of
      PCR amplified DNA

<400> SEQUENCE: 21
gctgtatcgt caaggcactc ttgcctacgc ca                                   32

<210> SEQ ID NO 22
<211> LENGTH: 66
<212> TYPE: DNA
<213> ORGANISM: Artificial
<220> FEATURE:
<223> OTHER INFORMATION: Synthetic oligonucleotide derived from Homo
      sapiens.

<400> SEQUENCE: 22
gctgtaaacg acggccagtt tcatgcaggg ctggagtcgt aggcaagagt gccttgacga     60
tacagc                                                               66

<210> SEQ ID NO 23
<211> LENGTH: 24
<212> TYPE: DNA
<213> ORGANISM: Artificial
<220> FEATURE:
<223> OTHER INFORMATION: Synthetic oligonucleotide derived from Homo
      sapiens.

<400> SEQUENCE: 23
gctgtaaacg acggccagtt tcat                                            24

<210> SEQ ID NO 24
<211> LENGTH: 66
<212> TYPE: DNA
<213> ORGANISM: Artificial
<220> FEATURE:
<223> OTHER INFORMATION: Nucleic acid derived from Homo sapiens and
      generated by primer extension

<400> SEQUENCE: 24
gctgtatcgt caaggcactc ttgcctacgc caccagccct gcatgaaact ggccgtcgtt     60
tacagc                                                               66

<210> SEQ ID NO 25
<211> LENGTH: 66
<212> TYPE: DNA
<213> ORGANISM: Artificial
<220> FEATURE:
<223> OTHER INFORMATION: Synthetic oligonucleotide derived from Homo
      sapiens.

<400> SEQUENCE: 25
gctgtaaacg acggccagtt tcatgcagga tccatggcgt aggcaagagt gccttgacga     60
tacagc                                                               66

<210> SEQ ID NO 26
```

```
<211> LENGTH: 66
<212> TYPE: DNA
<213> ORGANISM: Artificial
<220> FEATURE:
<223> OTHER INFORMATION: Nucleic acid derived from Homo sapiens and
      generated by primer extension

<400> SEQUENCE: 26
gctgtatcgt caaggcactc ttgcctacgc catggatcct gcatgaaact ggccgtcgtt     60
tacagc                                                                66

<210> SEQ ID NO 27
<211> LENGTH: 20
<212> TYPE: DNA
<213> ORGANISM: Artificial
<220> FEATURE:
<223> OTHER INFORMATION: Synthetic oligonucleotide derived from Homo
      sapiens.

<400> SEQUENCE: 27
ggtagttgga gctggtggcg                                                 20

<210> SEQ ID NO 28
<211> LENGTH: 10
<212> TYPE: DNA
<213> ORGANISM: Artificial
<220> FEATURE:
<223> OTHER INFORMATION: Synthetic oligonucleotide derived from Homo
      sapiens.

<400> SEQUENCE: 28
tccaactacc                                                            10

<210> SEQ ID NO 29
<211> LENGTH: 47
<212> TYPE: DNA
<213> ORGANISM: Artificial
<220> FEATURE:
<223> OTHER INFORMATION: Nucleic acid derived from Homo sapiens and
      generated by ligation of two DNA molecule

<400> SEQUENCE: 29
gctgtatcgt caaggcactc ttgcctacgc caccagctcc aactacc                   47

<210> SEQ ID NO 30
<211> LENGTH: 10
<212> TYPE: DNA
<213> ORGANISM: Artificial
<220> FEATURE:
<223> OTHER INFORMATION: Synthetic oligonucleotide derived from Homo
      sapiens.

<400> SEQUENCE: 30
ccagctccaa                                                            10

<210> SEQ ID NO 31
<211> LENGTH: 20
<212> TYPE: DNA
<213> ORGANISM: Artificial
<220> FEATURE:
<223> OTHER INFORMATION: Synthetic oligonucleotide derived from Homo
      sapiens.

<400> SEQUENCE: 31
ttggagctgg tggcgtaggc                                                 20
```

-continued

```
<210> SEQ ID NO 32
<211> LENGTH: 42
<212> TYPE: DNA
<213> ORGANISM: Artificial
<220> FEATURE:
<223> OTHER INFORMATION: Nucleic acid derived from Homo sapiens and
      generated by ligation of two DNA molecule

<400> SEQUENCE: 32
gctgtatcgt caaggcactc ttgcctacgc caccagctcc aa                          42
```

METHOD FOR THE CHARACTERIZATION OF NUCLEIC ACID MOLECULES INVOLVING GENERATION OF EXTENDIBLE UPSTREAM DNA FRAGMENTS RESULTING FROM THE CLEAVAGE OF NUCLEIC ACID AT AN ABASIC SITE

This application is the national phase under 35 U.S.C. § 371 of PCT International Application No. PCT/IE98/00030 which has an International filing date of Apr. 22, 1998, which designated the United States of America.

TECHNICAL FIELD

The present invention relates to a method for characterising nucleic acid molecules which involves generating extendible upstream DNA fragments which result from the cleavage of nucleic acid at an abasic site.

BACKGROUND ART

Characterisation of target nucleic acids is highly important for several reasons relating to confirmation of the presence or absence of a gene in a sample, confirmation of part or all of a nucleic acid sequence, and screening for the presence of known and unknown disease causing mutations leading to inherited disease and natural variations in DNA. Although there are many known methods for characterising nucleic acid and for the detection of unknown sequence changes, the increasing amount of new genetic information being generated makes it important to develop new, better and faster methods for characterisation of nucleic acids.

WO 97/03210 discloses the use of a DNA-glycosylase enzyme, which recognises a modified base, for the direct detection of known and unknown mutations in a target nucleic acid sample. The method typically involves amplifying a target nucleic acid sample using a combination of normal DNA precursor nucleotides and one or more modified precursor nucleotide(s) where the modified precursor nucleotide replaces one of the normal precursor nucleotides which is a substrate for a DNA glycosylase. Following excision of the modified base by the glycosylase, the resulting abasic site is cleaved and the products of the cleavage are analysed. This method allows detection of mutations at candidate loci. However, the method of WO 97/03210 has certain limitations. For example, with this method it is not possible to detect sequence differences between nucleic acid molecules without detecting sequence similarities and thus multiple samples cannot be combined for simultaneous analysis.

DISCLOSURE OF INVENTION

The invention provides a method for characterising nucleic acid molecules, which comprises the steps of:

i) introducing a modified base which is a substrate for a DNA glycosylase into a DNA molecule;

ii) excising the modified base by means of said DNA glycosylase so as to generate an abasic site;

iii) cleaving the DNA at the abasic site so as to generate an upstream DNA fragment that can be extended; and iv) incubating the extendible upstream fragment in the presence of an enzyme allowing for extension thereof and a template nucleic acid and analysing the resultant fragment(s).

The invention provides a novel, versatile and simple method using the above-mentioned extendible upstream DNA fragments which allows characterisation of nucleic acids and which has advantages over existing methods as indicated in the following description.

One of the most important uses (but not the only use) of the method according to the invention is to scan or check a fragment of DNA (target nucleic acid) for the presence or absence of a mutation. The method essentially consists of i) the generation of the extendible upstream DNA fragments and ii) the subsequent use of these fragments in analysing a piece of DNA (e.g. detecting a mutation).

Preferably, the modified base used is uracil, hypoxanthine or 8-OH guanine.

Preferably, the modified bases are derived from modified precursor nucleotides which when incorporated into DNA generate said modified bases.

Thus, the preferred modified precursor nucleotides are dUTP, dITP and 8-OH dGTP which when incorporated into DNA generate the glycosylase substrate bases uracil, hypoxanthine and 8-OH guanine, respectively. Each of the modified precursor nucleotides is a base sugar phosphate comprising said base and a sugar phosphate moiety. Uracil in DNA is recognised specifically by uracil DNA-glycosylase (UDG) and released from DNA. UDG also recognises other uracil related bases when present in DNA. Hypoxanthine is recognised specifically by alkylpurine DNA-glycosylases (ADG) and released from DNA. This enzyme also recognises and releases N3 methyladenine, N3 methylguanine, $O^2$ methylcytosine and $O^2$ methylthymine when present in DNA. 8-OH guanine is recognised specifically by formamido-pyrimidine DNA-glycosylase (FPG) and released from DNA. This enzyme also recognises and releases ring opened purines when present in DNA. Thymine DNA glycosylase recognises and releases uracil and thymine positioned opposite guanine bases in DNA.

Modified precursor nucleotide(s) as used herein refers to a modified nucleotide or nucleotides that can be incorporated into a nucleic acid so that a modified base or bases is generated which is/are recognised and can be excised by a DNA glycosylase enzyme.

Following the introduction of the modified base, the DNA product is treated with a suitable DNA glycosylase enzyme which recognises and releases the glycosylase substrate base present in the target sample and consequently generates an apurinic or apyrimidinic (AP) site, depending on the nature of the modified base(s). AP site is the term given to a site in DNA where the base moiety of a nucleotide has been lost or removed, leaving behind a deoxyribophosphate with the DNA phosphodiester backbone still intact. AP is the abbreviation for either apurinic and/or apyrimidinic depending on whether a purine or pyrimidine base had been attached to the ribose ring. An AP site is also referred to as an abasic site, being the general term for apurinic and apyrimidinic site.

Release of the glycosylase substrate base from the nucleic acid sample results for example in an apyrimidinic site in the case of uracil and an apurinic site in the case of hypoxanthine and 8-OH dG. Collectively, such sites are referred to as abasic sites.

Essentially, cleaved fragments must have hydroxyl groups at the 3' termini and the DNA immediately downstream of said 3' termini must not be blocked in a way that prevents extension of the fragment from said 3' termini. Cleaved fragments are generated that have hydroxyl at the 3' termini and downstream blocking groups are removed that prevent extension of the fragment from the said 3' termini, while using as template, that DNA from which the extendible fragment was derived.

The DNA can be cleaved in a number of ways at the abasic site so as to generate said upstream DNA fragment as hereinafter described in greater detail.

For example, the phosphate linkages at the abasic sites can be cleaved by a treatment selected from treatment with a basic solution or other chemical treatment, heat treatment and/or treatment with an enzyme.

According to one embodiment of the invention, the upstream fragment is generated by cleaving the DNA at the 5' side of the abasic site such that the 3' terminus of the upstream fragment bears a hydroxyl group.

The terms extendible fragment and upstream DNA fragment are used interchangeably herein.

As the 3'-OH termini are thereby generated no further processing of the upstream fragments is required prior to step iv).

Treatment with basic solutions (alkali) at high temperature or with a chemical such as piperidine, or with an enzyme which cuts specifically at abasic sites, such as *E. coli* endonuclease IV results in cleavage of the abasic site on the 5' side.

Suitably in this embodiment, the cleavage is achieved with a 5' AP endonuclease.

According to an alternative embodiment the upstream fragment is generated by cleaving at the 5' side of the abasic site so as to leave a phosphate group at the 3' terminus of the upstream fragment and removing the phosphate group so that the upstream fragment bears a hydroxyl group at the 3' terminus.

Alternatively, cleavage with alkali or the abasic endonuclease activity of FPG is used, followed by removal of the 3' phosphate. For example 3' phosphate groups can be removed by enzymatic means using enzymes with 3' phosphate activity such as T4 polynucleotide kinase.

According to a still further embodiment, the upstream fragment is generated by cleaving at the 3' side of the abasic site so as to generate a deoxyribose group phosphate at the 3' terminus of the upstream fragment and subsequently removing the deoxyribose group to leave a hydroxyl group at the 3' terminus.

This can be achieved by using an enzyme with 3' deoxyribo-phosphodiesterase activity, or using FPG followed by a 3' phosphatase.

In an alternative embodiment 5' deoxyribose moieties downstream of the 3' terminus of the upstream fragment are removed so that the upstream fragment can be extended on the template.

Preferably the 5' deoxyribose moieties are removed by a 5' deoxyribophosphodiesterase.

Treatment with high temperature alone or a 3' AP endonuclease results in cleavage of the abasic site to completion on the 3' side.

Glycosylase mediated cleavage cuts the extended primer at an abasic site subsequent to release of the modified base by a DNA glycosylase yielding 3' termini with 3'-OH or 3' phosphate groups or deoxyribophosphate groups. Except in cases where 3'-OH termini are generated, all other termini require further processing prior to extension of the upstream fragment.

Glycosylase mediated cleavage in the method according to the invention refers to both 5' and 3' cleavage, including whatever subsequent treatment that is necessary to generate a 3' OH group at the 3' terminus of the upstream fragment.

Preferably, the modified base is introduced by enzymatic amplification of the DNA.

Preferably, the DNA (herein also referred to as target nucleic acid) is amplified using normal DNA precursor nucleotides and at least one modified precursor nucleotide.

Precursor nucleotides in the case of a DNA amplification process refer to the deoxyribonucleotides dATP, dCTP, dGTP and dTTP herein referred to as "normal" DNA precursor nucleotides.

The term "amplifying" as used herein refers to any in vitro process for increasing the number of copies of a nucleotide sequence or sequences. Amplification of a target nucleic acid molecule results in the incorporation of precursor nucleotides into the DNA being amplified. Typically, amplification of a target sample is carried out using appropriate primers in the polymerase chain reaction (PCR). During the amplification, primers anneal to the target nucleic acid and are extended using a DNA polymerase in a 5' to 3' direction on the target nucleic acid which acts as a template for synthesis of new DNA. The use of flanking primers, which are referred to herein as initial primers, which anneal to the upper and lower-strands of a DNA molecule permit exponential amplification of the DNA segment delimited by the upper and lower primers.

The amplification will typically involve amplifying a target nucleic acid using a combination of normal DNA precursor nucleotides and one or more modified precursor nucleotide(s) where the modified precursor nucleotide replaces all or a proportion of one of the normal precursor nucleotides. Amplification of a nucleic acid using normal DNA precursor nucleotides results in the incorporation of the four normal bases G,A,T, or C into DNA. Amplification of a nucleic acid using a modified precursor nucleotide in place of one of the normal precursor nucleotides results in the incorporation of a glycosylase substrate base into DNA in place of one of the four normal bases G,A,T, or C.

The target nucleic acid sample will typically be DNA. However, RNA may also be used following conversion to DNA by reverse transcription.

When a modified precursor nucleotide replaces a proportion of one of the normal precursor nucleotides, the ratio of the modified precursor nucleotide to the normal precursor nucleotide that it is replacing is such that an optimum of one modified precursor nucleotide is incorporated per strand of amplified DNA. This allows subsequent cleavage of the amplified DNA strand into two fragments following contact with a DNA glycosylase and an abasic site cleavage agent as herein described. This method of cleavage is herein referred to as glycosylase mediated cleavage. A higher ratio of the modified precursor nucleotide to normal precursor nucleotide is used to generate more than one cleavage site per amplified DNA strand. The incorporation of a modified precursor nucleotide into the amplified product generates one or more modified bases at one or more positions recognised by a DNA glycosylase enzyme in the amplified product.

Replacement of all of a normal precursor nucleotide with a modified precursor nucleotide in the amplification reaction if used in step i) permits glycosylase mediated cleavage of a primer extended in an amplification reaction at the first position 3' of the extended primer where a normal base is replaced by a modified base. Thus, if the template sequence immediately 3' of a location where the primer hybridises is CTAG and the modified nucleotide precursor is dUTP replacing dTTP, then the modified base uracil (U) will be incorporated opposite A on the template strand. Thus, in this situation, the primer will have been extended by two nucleotides at the 3' end (primer-GA 3') following amplification and glycosylase mediated cleavage. These extended primers generated following the initial extension and glycosylase mediated cleavage are referred to herein inter alia as extendible fragments, as indicated above, whereas the primers prior to extension are referred to as the initial primers herein.

The extended 3' terminal sequence of the extendible fragment is enzymatically synthesised and is directly related to the nucleic acid being characterised as the nucleic acid acts as the template for its synthesis. Thus the 3' end of the extendible fragment is complementary to the nucleic acid. Accordingly, determination of the nature of the 3' end of the extendible fragment by any means allows characterisation of the nucleic acid from which it was derived. If an initial primer is placed adjacent to a locus where a DNA sequence variation such as a polymorphism or a mutation occurs so that the first modified base incorporated into the extended primer is at the mutation locus, then the initial primer will be extended to a different length depending on whether or not a mutation is present at the mutation locus following glycosylase mediated cleavage. The extendible fragments are subsequently treated (if necessary) so that they can be used as primers for a subsequent extension reaction. Because the sequence at the 3' termini of the extendible fragments differ depending on whether a mutation is present or absent at the mutation locus, analysis of the ability of an extendible fragment to function in a subsequent extension reaction using a template nucleic acid permits the determination of whether a mutation is present or absent at the mutation locus. Any naturally occurring or enzymatically or chemically synthesised template which fully or partially hybridises to the extendible fragment can be designed and/or selected as a template nucleic acid allowing the ability of the extendible fragment to function as a primer to be determined.

When a proportion of a normal precursor nucleotide is replaced with a modified precursor nucleotide in the amplification reaction, glycosylase mediated cleavage of the primer extended in an amplification reaction will yield a population of extendible fragments of various lengths since different molecules will be cleaved at different points depending on where the modified precursor nucleotide is incorporated. The length of each fragment is determined by the position of incorporation of the modified precursor nucleotide during extension from the 3' end of the initial primer.

Amplification of a target nucleic acid using the precursor nucleotides dATP, dCTP, dGTP, dTTP and a low amount of the modified precursor nucleotide dUTP results in an amplified DNA where thymine is replaced randomly by uracil. The uracil is incorporated in the newly synthesised DNA strand at positions complementary to adenine residues in the template DNA strand during the amplification process. Amplification of a target nucleic acid using the precursor nucleotides dATP, dCTP, dGTP, dTTP and a low amount of the modified precursor nucleotide dITP results in an amplified DNA where guanine is preferentially replaced randomly by hypoxanthine. The hypoxanthine is incorporated in the newly synthesised DNA strand at positions complementary to cytosine residues in the template DNA strand during the amplification process when the other precursor nucleotides are not limiting. Amplification of a target nucleic acid using the precursor nucleotides dATP, dCTP, dGTP, dTTP and a low amount of the modified precursor nucleotide 8-OH dGTP results in an amplified DNA where guanine is preferentially replaced randomly by 8-OH guanine. The 8-OH guanine is incorporated in the newly synthesised DNA strand at positions complementary to cytosine residues in the template DNA strand during the amplification process when the other precursor nucleotides are not limiting.

The amplified DNA strands can be separated for separate analysis of the respective strands. In addition, the separated strands can be immobilised, which can be achieved by several means. A common method for immobilisation and/or separation of DNA strands is by the use of the biotin streptavidin interaction, where normally, the DNA contains the biotin label and the streptavidin is attached to a solid support. However, the method according to the invention in its various steps is amenable to immobilisation formats that allows immobilisation of the upstream fragment, the strand bearing the upstream fragment, the strand complementary to the strand bearing the upstream fragment, the template nucleic acid, the target nucleic acid and the products generated from glycosylase mediated cleavage of amplified or extended nucleic acids bearing modified bases.

The modified base can be introduced by chemical modification of a nucleic acid, rather than by an amplification technique such as PCR.

Several methods exist where the treatment of DNA with specific chemicals modifies existing bases so that they are recognised by specific DNA glycosylase enzymes. For example, treatment of DNA with alkylating agents such as methylnitrosourea generates several alkylated bases including N3-methyladenine and N3-methylguanine that are recognised and excised by alkyl purine DNA-glycosylase. Treatment of DNA with sodium bisulfite causes deamination of cytosine residues in DNA to form uracil residues which are recognised and excised by uracil DNA-glycosylase. Treatment of DNA with ferrous sulphate and EDTA causes oxidation of guanine residues in DNA to form 8-OH guanine residues in DNA which are recognised and excised by formamido-pyrimidine DNA glycosylase.

Thus, bases present in the nucleic acid or indeed, the extendible upstream fragment generated in step iii) can be converted into modified bases by chemical means. A proportion or all of the cytosine residues can be readily converted to an uracil using sodium bisulfite thereby rendering the amplified sample susceptible to uracil DNA-glycosylase cleavage at the sites of cytosine conversion. If the upper or lower primer is synthesised so that it contains 5-methylcytosine rather than cytosine, in such a case the primer will be resistant to uracil DNA-glycosylase mediated cleavage since deamination of 5-methylcytosine occurs at a reduced rate by comparison with cytosine and generates a thymine rather than an uracil residue.

Prior to treatment with a suitable DNA glycosylase, double stranded DNA may be treated with exonuclease I. This treatment serves to digest the unused primers and any non-specific single stranded DNA amplification products thus improving the signal to noise ratio.

In the case where the modified precursor nucleotide is dUTP, the modified base uracil will be generated at thymine positions in the amplified target nucleic acid sample. Addition of uracil DNA-glycosylase to the sample releases the uracil from the sample. In the case where the modified precursor nucleotide is dITP, the modified base hypoxanthine will be generated at guanine positions in the amplified target nucleic acid sample. Addition of alkylpurine DNA-glycosylase to the sample releases the hypoxanthine from the sample. In the case where the modified precursor nucleotide is 8-OH dGTP, the modified base 8-OH guanine will be generated at guanine positions in the amplified target nucleic acid sample. Addition of formamido-pyrimidine DNA-glycosylase to the sample releases the 8-OH guanine from the sample.

Suitably a primer or one or more nucleotide(s) involved in the enzymatic amplification is labelled.

The initial primer used may be suitably labelled. Labelling of the primers can be performed by a variety of means including addition of a radioactive, fluorescent, or detectable ligand to the primer during or post primer synthesis.

In one embodiment of the invention, the enzyme used in step iv) is a polymerase which can be incubated with the extendible upstream fragment in the presence of one or more nucleotide(s).

Also in this embodiment suitably one or more of the nucleotide(s) of step iv) is a dideoxy nucleotide.

Also one or more of the nucleotides of step iv) can be labelled.

Various nucleic acid polymerases can be used to extend the 3' terminus of the extendible fragment on a template nucleic acid. Many polymerases are described in the literature that extend 3' termini of primers on a template DNA. For example, DNA polymerases isolated from phage and mesophilic and thermophilic bacteria can be used.

Several DNA polymerases, including T7 DNA polymerase incorporate dideoxy terminator nucleotides as a well as normal precursor nucleotides during extension of primers. Thermophilic DNA polymerases are used routinely in amplification of nucleic acids through repeated cyclic extension of primers. The upstream DNA fragments generated in step iii) function as primers for all nucleic acid polymerases capable of extending standard nucleic acid primers.

The use of a labelled precursor nucleotide or dideoxy terminator nucleotide in any of the extension reactions facilitates detection of the extended extendible fragment. Direct DNA staining methods such as silver or ethidium bromide staining facilitate detection of all extension products after size separation based on electrophoretic mobility.

The ability of the extendible fragments to function in a subsequent extension reaction using a template nucleic acid and normal or dideoxy terminator nucleotides (a nucleotide that prohibits further extension of a primer on a template once incorporated) generates a ladder of fragments allowing determination of the location of the total number of positions of the modified precursor nucleotide in one or both strands of the amplified target nucleic acid. The presence of a sequence variation or mutation results in the appearance or disappearance of a cleavage fragment as judged by comparison with the known DNA sequence of the amplified molecule. Size analysis of the fragments allows the precise location and sequence of a mutation in the target nucleic acid sample to be determined. Therefore, if a sequence variation occurs such that an additional site of modified precursor nucleotide incorporation is generated, an additional cleavage fragment will be observed upon analysis of the ladder of cleavage products. If a sequence variation occurs such that a site of modified precursor nucleotide incorporation is lost, the corresponding cleavage fragment will not be observed upon analysis of the ladder of cleavage products.

The template of choice in this case will be the originally intact or glycosylase cleaved amplified nucleic acid. In cases where glycosylase cleaved amplified nucleic acid is used it can be processed to remove residual moieties downstream of the extendible fragment which prohibit extension of the extendible fragment by a nucleic acid polymerase. Specifically the template DNA can be treated so that a residual 5' deoxyribose moiety is removed. This is achieved by incubation of the template DNA with a 5' deoxyribophosphodiesterase such as E. coli RecJ endonuclease or formamidopyrimidine DNA glycosylase. Other naturally occurring or enzymatically or chemically synthesised template nucleic acids which fully or partially hybridise to the extendible fragment can also be designed and/or selected as a template nucleic acid to determine the ability of the extendible fragment to function as a primer.

The ability of the extendible fragments to function in a subsequent extension reaction using a template nucleic acid and a combination of non-labelled and labelled normal or dideoxy terminator nucleotides permits detection of sequence variations and mutations. Extension of the extendible fragments on the template nucleic acid from which they were derived and which is heterozygous for the sequence variation, using a labelled dideoxy terminator nucleotide having base pairing properties different to those of the modified precursor nucleotide with a non-labelled dideoxy terminator nucleotide having the same base pairing properties as the modified precursor nucleotide allows detection of the variant or mutant loci alone whereas non variant loci are not detected. This aspect of the invention is particularly advantageous as detection of sequence variations alone permits very high throughput mutation scanning and detection, and allows fingerprinting of nucleic acids based on their sequence variations.

It will be appreciated that amplification of any target DNA, which is heterozygous for a mutation or polymorphism generates four distinct duplex DNAs, i.e. (taking as an example a G to A mutation at position X in a DNA sequence), one quarter will be homoduplex with a GC base pair at position X, one quarter will be homoduplex with an AT base pair at position X, one quarter will be heteroduplex with a GT base pair at position X, and one quarter will be heteroduplex with a AC base pair at position X. Similarly, heteroduplex DNA can be generated readily by denaturing and reannealing two homoduplex DNAs bearing a sequence difference(s).

Thus, the nature of the sequence of the 3'end of the extendible fragments can be determined by their ability to function as primers in a subsequent extension reaction using a template nucleic acid. Essentially, such determination is based on the ability of the 3'end of the extendible fragment to hybridise to a selected template under selected conditions. Following partial or complete hybridisation the extendible fragment may be extended using a nucleic acid polymerase and nucleic acid precursors or selected combinations of same as herein described. It will be appreciated that multiple possibilities exist for the selection of template molecules. Nonetheless, the extension of the extendible fragment is a measure of its hybridisation to or lack of hybridisation to a selected template molecule and thus the determination of the nature of the sequence of the 3'end of the extendible fragments is made on this basis, since this 3' sequence is indicative of the sequence of the original target nucleic acid.

Typically, the template molecule is selected so that it bears partial or full sequence complementarity to the upstream fragment. The upstream fragment may be extended one or more nucleotides on the template molecule using a nucleic acid polymerase and nucleic acid precursors or a combination of same or dideoxy terminator nucleotides or a combination of normal nucleic acid precursors and dideoxy terminator nucleotides.

The extension of step iv) can be achieved by means of an amplification reaction using said extendible DNA fragment.

Alternatively, the extension of step iv) is achieved by means of an amplification reaction including a primer in addition to using said extendible DNA fragment.

Repeated extension of an upstream fragment on a template nucleic acid in combination with a second flanking primer which can be extended on the copy of the template permits amplification of the template nucleic acid. Such amplified products can be readily detected by standard nucleic acid staining methods such as ethidium bromide after resolution by electrophoresis.

Alternatively, the template molecule may be selected so that it can be extended using the upstream fragment as a template and so that the extension is based on hybridisation to the 3' end of the upstream fragment.

Also, the upstream fragment may be analysed based on its ability to function in a 5' nuclease assay. During extension of the upstream fragment by a polymerase with 5' to 3' nuclease activity, the 5' to 3' nuclease activity degrades a downstream reporter molecule annealled to the same template strand as said upstream fragment.

A further possibility is for the upstream fragment to be extended on a synthetic template which contains reporter and quencher labels, then cleavage of the resulting double stranded DNA will release the reporter from the quencher and a signal will be detected. Typically such cleavage will be carried out by an enzyme which recognises the double stranded DNA molecule. Typically such an enzyme will be a restriction enzyme.

Furthermore, the 3' terminal sequence of the upstream fragment may be determined on the basis of its hybridisation to other nucleic acid molecules.

A further possibility is that the products extended or amplified using upstream fragments may be detected on the basis of their filtration and/or precipitation properties.

When analysing extension and incorporation of nucleotides in step iv) where the upstream fragments are used in an extension reaction, it is important to verify that any extension observed is specifically due to extension of the upstream fragments and not due to extension of the initial primers which were unused during the initial amplification, if such is used in step i), or extension of possible non-specific upstream fragments which may be generated by the non-specific breakage or damage of the DNA during previous steps of the procedure. To overcome this 'noise', the DNA, prior to glycosylase mediated treatment, can be treated with a single strand specific DNA nuclease, for example, Exonuclease I, which will degrade the unused primers and non-specific single stranded DNA and can be subsequently heat inactivated. The DNA can be treated with a 3' AP endonuclease/lyase which will cut the DNA and primers at any preexisting AP sites, generated specifically or generated through damage of the DNA. The 3' AP endonuclease/lyase is subsequently removed from the reaction. Because the endonuclease/lyase cuts at the 3' side, the resulting contaminating upstream fragments are not extendible and will not interfere with the extension of the subsequently generated upstream fragments. In addition to these treatments, a control reaction to check for non-specific extensions can be carried out. Thus, in step iii) of the method, the AP sites can be cut with a 3' AP endonuclease/lyase, thereby generating non-extendible upstream fragments. If however, extension and incorporation of nucleotides is observed in the subsequent step iv) then one can measure or determine the level of non-specific extension obtained during the procedure.

Similarly it is important to ensure that the incorporation of nucleotides, labelled or unlabelled, in step iv) is due to the incorporation of those nucleotides supplied during step iv) and not those from any previous step. This is especially important when the reaction involves incorporation of dideoxynucleotides. Prior to or subsequent to cleaving the DNA at abasic sites and generating upstream fragments, the reaction can then be treated with a phosphatase which digests all unincorporated nucleotides present in the reaction, e.g. shrimp alkaline phosphatase, which can subsequently be heat inactivated.

In a further embodiment of the invention, the enzyme used in step iv) is a ligase which can be incubated with the extendible upstream fragment in the presence of a reporter oligonucleotide.

The reporter oligonucleotide may be partially degenerate.

The method according to the invention can be used inter alia to detect a known or unknown mutation and to detect differences and similarities in genomes. These aspects of the invention are illustrated further below.

The method according to the invention provides in one aspect a means of generating random primers in a simple easy manner. Essentially, introduction of a modified base into an amplified DNA product followed by glycosylase mediated cleavage and subsequent treatment of the cleavage products so that they can be extended by a nucleic acid polymerase provides a rapid means of generating random primers. Subsequent use of such primers, i.e., the extendible upstream fragments, in random amplification of target nucleic acids allows amplification of discrete DNA molecules from the target nucleic acids thus permitting characterisation of the nucleic acid based on similarities and differences of the amplified products. Since these primers are essentially derived from said target nucleic acid, specifically their 3' ends, they are better primers for the subsequent random amplification analysis of said target nucleic acid and the amplification is more specific. Many discrete DNA products are generated during random amplification of nucleic acids. A discrete DNA product can be separated from other products on the basis of size. The method according to the invention permits the generation of primers from all or part of the separated product. Use of an initial primer in the random amplification of a nucleic acid that permits immobilisation of the separated product allows the isolation of the upper and lower primers extended to the first point of glycosylase mediated cleavage. The 3' end of such upstream fragments are derived from the target nucleic acid and thus permit more specific amplification of the target nucleic acid or related nucleic acids. The 3' end of such upstream fragments may be short or long. By short 3' ends herein is meant one to three nucleotides whereas by long 3' ends herein is meant greater than three nucleotides. Longer 3' ends on such upstream fragments are more desirable as they allow highly specific amplification of a target nucleic acid sequence. Upstream fragments generated with longer 3' ends may be selected by sizing methods. Alternatively, the initial amplification primers can be designed so that they promote binding of a protein that protects a section of the region 3' of the initial extended primer. Thus such a region is refractory to glycosylase mediated cleavage due to protection by the protein and inclusion of such a primer design and protein allows generation of upstream fragments with longer 3' ends.

This embodiment of the invention provides a rapid and simple method for generation of random and specific primers for nucleic acid amplification without prior knowledge of the nucleic acid sequence.

It will be appreciated that the random amplification of nucleic acid using arbitrarily chosen primers is a method already known for detecting similarities and differences between genomes. Such random amplification is based on the annealing of arbitrarily chosen primers to target samples followed by multiple rounds of enzymatic amplification whereby the primers are extended using the selected genomic DNA or cDNA as template. Using such primers in such a method results in the amplification of discrete DNA molecules. Analysis of such molecules allows the investigation of similarities and differences between different samples. Typically many different random primers are chosen for investigation of a genome or cDNA and such primers are synthesised chemically and are designed in a random fashion with the assumption that they will hybridise to the target nucleic acid in the amplification process. The method according to the invention allows the easy and rapid generation of primers from a target nucleic acid which can subsequently be used for random amplification of the same or different target nucleic acid.

In addition to extension by a polymerase reaction, as indicated above, the upstream fragments in step iv) can also be extended by ligation of another single stranded DNA molecule which results in extended upstream fragments greater in size than the initial upstream fragments generated by glycosylase mediated cleavage. The DNA molecule to which the upstream fragment is ligated is termed the reporter oligonucleotide herein and this can vary in length. Ligation of the upstream fragments to the reporter oligonucleotide is dependent on both DNA molecules (the upstream fragment and reporter oligonucleotide) annealing to a template molecule at adjacent sites so that the termini of the upstream fragment and reporter oligonucleotide are juxtaposed. This means that the 3' terminal base of the upstream fragment is juxtaposed to the 5' terminal base of the reporter oligonucleotide. The reporter oligonucleotide is typically a synthetic oligonucleotide, but can also be any other type of DNA molecule or RNA molecule.

The template molecule is selected so that it bears partial or full sequence complementarity to the upstream fragment and reporter oligonucleotide. The template of choice can be the originally intact or glycosylase cleaved amplified nucleic acid. In addition the template can be a single stranded DNA molecule, e.g. synthetic oligonucleotide, which can vary in length and which will allow complementary annealing of the upstream fragment(s) and reporter oligonucleotide(s). The template DNA can be single stranded or double stranded in nature. Double stranded DNA acting as template consists of the template strand and the complementary strand. Double stranded DNA must first be denatured and then allowed to reanneal in the presence of the upstream fragment and reporter oligonucleotide. The upstream fragment and reporter oligonucleotide then compete with the complementary strand in annealing to the template strand of the double stranded template molecule.

Various DNA ligases and RNA ligases can be used to extend the 3' terminus of the extendible fragment by ligation of a reporter oligonucleotide on a template nucleic acid. DNA ligases from many sources, including those isolated from phage, e.g. T4 DNA ligase, and mesophilic and thermophilic bacteria, can be used to ligate the reporter oligonucleotide to the extendible fragment. Thermophilic DNA ligases can be used in repeated cyclic ligations of the extendible fragments to reporter oligonucleotides.

As discussed above, the method according to the invention involves the production of an upstream fragment which has a 3' hydroxyl group. This is an essential requirement for extension of the molecule by addition of nucleotides by a polymerase and also for extension by ligation of a reporter oligonucleotide by a ligase. In addition to a 3' hydroxyl group on the upstream fragment, the reporter oligonucleotide is required to have a 5' phosphate group for ligation to occur. Ligation, in addition, allows detection of the downstream fragment if desired. The downstream fragment is the remainder of the DNA strand from which the upstream fragment was cleaved. Here, the reporter oligonucleotide is required to have a 3' hydroxyl terminus and the downstream fragment to have a 5' terminal phosphate group.

Since glycosylase mediated cleavage may generate several different upstream fragments in an individual reaction due to the presence of normal and mutant alleles in the target nucleic acid or due to the random introduction of modified bases, the extension by ligation reaction may contain several different upstream fragments in addition to several different reporter oligonucleotides and template nucleic acids. In addition several different nucleic acids may be characterised simultaneously since an individual reporter oligonucleotide and/or template nucleic acid may be used for the characterisation of each individual nucleic acid under investigation. The extended upstream fragment can be detected by any of several means including size analysis, hybridisation and amplification. In addition, the DNA molecule resulting from ligation can be further amplified in a polymerase chain reaction.

The reporter oligonucleotide, upstream fragment or template nucleic acid may be labelled. For example a fluorescent or radioactive label may be used in addition to a biotin or digoxigenin label. A useful label on the reporter oligonucleotide is a 5' terminal radioactive phosphate, i.e. $^{32}$P or $^{33}$P. This radioactive phosphate serves as a label with which to detect the DNA and also as the necessary 5' phosphate on the reporter molecule. A biotin label on the reporter oligonucleotide, upstream fragment or template nucleic acid will serve to immobilise the extended upstream fragment directly, or via hybridisation, to a solid support. Immobilisation, in combination with multiple different ligation extensions will serve to produce a very efficient and high throughput system for characterisation of DNA molecules.

The invention, using extension by ligation, may also be used to identify unknown sequence changes in nucleic acid by its ability to identify a mutant upstream fragment in a mixture of normal upstream fragments. A partially degenerate reporter oligonucleotide may be used in the ligation reaction. Selective ligation of an upstream fragment arising from cleavage of a DNA molecule at a mutation site can also be achieved by using a degenerate reporter oligonucleotide where the 5' terminus is complementary to the normal allele. In addition the invention can be used to investigate all CpG dinucleotide sites within a DNA fragment by using a fully complementary reporter oligonucleotide designed to anneal at each CpG site. The length of any resulting ligation product will indicate the CpG site which has been mutated.

Suitably, any extended fragments resulting from step iv) are detected by hybridisation.

The method according to the invention offers significant advantages over existing methods in that a) it allows detection of the similarities or the differences, or the similarities and differences between nucleic acid samples. In particular, it allows the detection of same at large numbers of multiple different loci in a nucleic acid. While it is possible to use other methods to achieve this end point, this method offers the advantage of a single process which can readily be scaled up allowing rapid and easy characterisation of nucleic acid molecules.

b) It will be appreciated that amplification of nucleic acids is a common method for characterising and detecting nucleic acids. Amplification is dependent on the use of primers which are extended in the amplification process. In addition, the method according to the invention allows the generation of high specificity primers for amplification of nucleic acids without the necessity of prior knowledge of any of the sequence of the nucleic acid. Thus, the present method has a high utility for the characterisation of nucleic acids through analysis of amplification products generated therefrom. The amplification approaches described for characterising nucleic acids according to the invention allow characterisation of nucleic acids in a way that was not possible prior to the present invention.

c) in the field, there is a need for simplified methods for the detection of specific mutations at candidate loci. The method according to the invention offers such a simplified method for the detection of such mutations. In particular, the upstream fragment generated from sequence variation loci in nucleic acids allow the analysis of such loci using many different analytical approaches and allow accurate and simplified detection of sequence variations at such loci.

d) the method according to the invention offers a more reproducible method for characterising nucleic acids by random amplification and is less susceptible to error.

The method according to the invention can also be used to analyse the CpG content of DNA by detecting C to T transitions in DNA.

Upon analysis of mutation data and mutation spectra that have been generated over many years of mutation research, a definite hotspot for mutations in all organisms which contain 5-methylcytosine in their genomic DNA e.g. humans, has been identified, namely, mutations at CpG dinucleotides. CpG dinucleotides are a site for cytosine methylation in human cells and have been implicated in many structural and regulatory roles in genome organisation and gene expression, respectively. Cytosine in DNA is normally susceptible to a low but measurable level of deamination to form uracil, an event which is mutagenic if not repaired. However, upon methylation at the 5' site, the cytosine ring now is even more susceptible to spontaneous deamination. Therefore, the 5-methylcytosine residue is deaminated to become thymine. Following deamination, the CpG dinucleotide becomes a TpG dinucleotide. Therefore, since 5-methylcytosine occurs only at a CpG, and the major cause of mutation at this site is due to deamination of the 5-methylcytosine, mutated CpG sequences appear in DNA as TpG dinucleotide sequences which represents a classic C to T transition mutation. Since CpG has been demonstrated to be such a hotspot for mutation in human genetic studies, a rapid screen for enhanced detection of mutations at CpG dinucleotides within the test fragment of DNA is highly advantageous.

To enhance the detection of mutations at CpG sequences, one of the following procedures can be carried out subsequent to amplification of the target DNA followed by cleavage to generate the upstream fragments.

Step iv) is carried out in the presence of a polymerase, dideoxyTTP(ddTTP), labelled dideoxy CTP(ddCTP) and wild type DNA as template, the upstream fragments are extended by incorporation of dideoxynucleotides, but only sites where C has mutated to T, including sites where CpG has mutated to TpG will become labelled following the incorporation of the labelled ddCTP. Since the ddCTP is a chain terminator nucleotide, the DNA will not be extended beyond this point. Therefore the DNA will be extended at mutated CpG sequences and will also be labelled and detectable.

Step iv) is carried out in the presence of a polymerase, wild type DNA as template, dTTP and labelled dideoxyGTP (ddGTP), the upstream fragments are extended by incorporation of dTMP, but only sites where the T is followed by G, i.e. TpG sequences will become labelled following the incorporation of the labelled ddGTP. Since the ddGTP is a chain terminator nucleotide, the DNA will not be extended beyond this point. Therefore the DNA is now extended at all TpG sequences and is also labelled and detectable. Since TpG dinucleotides occur naturally in DNA as well as arising from CpG deamination, wild type DNA will show a characteristic banding pattern (normally only a few bands will be seen). The label can be e.g. radioactive $^{33}$P, fluorescent, or biotin labelled in a manner known per se.

Step iv) is carried out in the presence of polymerase, dUTP, dGTP, dATP, labelled dCTP and wild type DNA as template, the upstream fragments are extended by incorporation of deoxynucleotides and become labelled. The extended upstream fragments are subsequently cleaved by uracil DNA glycosylase and abasic site cleavage agent. Only that upstream fragment which was generated by cleavage at the mutation site will remain extended and labelled. This procedure will detect all mutations generating a T incorporation site including C to T mutations at CpG sites. This procedure has the advantage that step iv) utilises the incorporation of deoxynucleotides which are incorporated more efficiently than dideoxynucleotides by all polymerases.

In addition, in heterozygous samples, the mutated CpG will give rise to T/G mismatches (or U/G after introduction of dUTP as modified nucleotide). The thymine DNA glycosylase can be used to specifically cleave at these T/G or U/G mismatches at a mutated CpG sequence.

BRIEF DESCRIPTION OF DRAWINGS

FIG. 3 is a schematic representation of the method according to the invention as described in Example 2 where a labelled ddTTP was used in a linear amplification reaction following generation of an upstream extendible fragment;

FIG. 4 is a schematic representation of the method according to the invention as described in Example 2 where a labelled ddCTP was used in a linear amplification reaction following generation of an upstream extendible fragment;

FIG. 5 is a schematic representation of the method according to the invention as described in Example 3;

FIGS. 6A–6D is a schematic representation of the extension products obtained in Example 3 following electrophoresis and autoradiography and analysis of the autoradiographs.

FIG. 1 depicts a single strand of DNA in 5' to 3' orientation. The position of two bases is shown, i.e. base 1 and base 3. Base 2 has been removed and an AP site exists at this position. The vertical lines denote the ribose ring which is attached to the base. The diagonal lines with 'P' in a circle refer to the phosphodiester linkages linking each ribose. The DNA can be cut at the 5' side or 3' side of an AP site as shown by arrows. If the DNA is cleaved at the 3' side of the AP site, i.e. position Z, then the upstream fragment (containing base 1) has a deoxyribose phosphate moiety at its 3' terminus as shown in box C. Cleavage of the DNA at the 3' side of the AP site can be achieved by treatment with a 3' AP endonuclease/lyase or heat treatment as hereinabove described.

The AP site can also be cut in two different ways on the 5' side of the AP site, i.e. at positions X and Y. Cleavage at position X results in a OH group at the 3' terminus on the upstream fragment, as shown in box A. Cleavage at position X can be achieved by treatment with a 5' AP endonuclease as hereinabove described. Cleavage at position Y results in a phosphate group at the 3' terminus of the upstream fragment, as shown in box B. Cleavage at position Y can be achieved by treatment with heat and alkali as hereinabove described.

The invention will be further illustrated by the accompanying Examples.

MODES FOR CARRYING OUT THE INVENTION

Example 1

The method according to the invention was used to demonstrate the production of an extended DNA fragment by extension from the 3'OH group of an upstream fragment, which had been generated by cleavage of uracil containing DNA at the site of incorporation of the modified nucleotide. Target nucleic acid was a region of the RYR1 gene (952 to 1044) amplified from human cDNA by using upper (952 to 972) and lower (1024 to 1044) primers to generate a double stranded DNA, 93 bp in length. (Nucleotide numbers refer to the sequence of the RYR1 gene)

Figure 1:
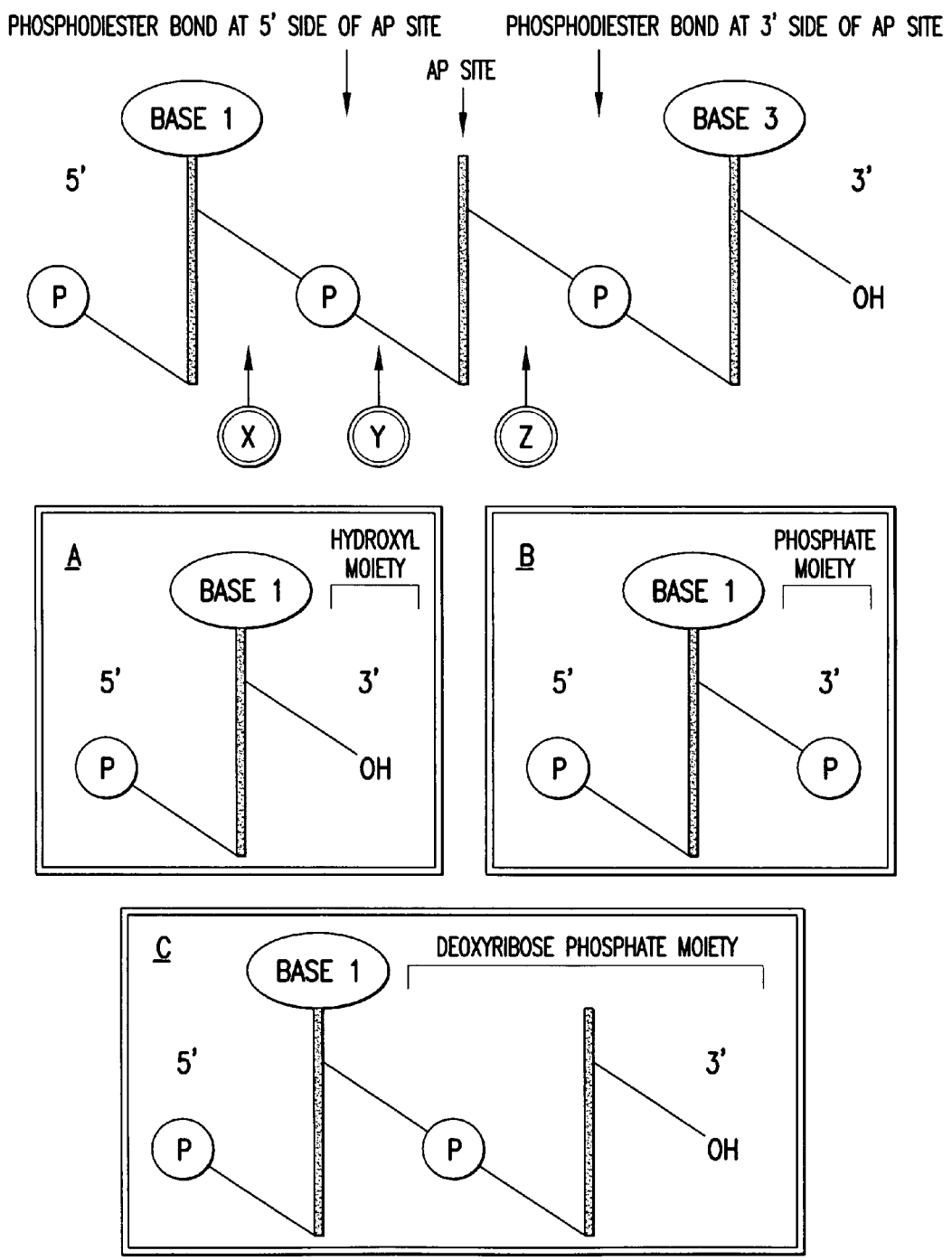
FIG. 1 is a diagram of an AP site generated during one step of the method according to the invention and of a number of ways in which the DNA at the abasic site can be cleaved so as to generate an upstream DNA fragment that can be extended.
Figure 2:
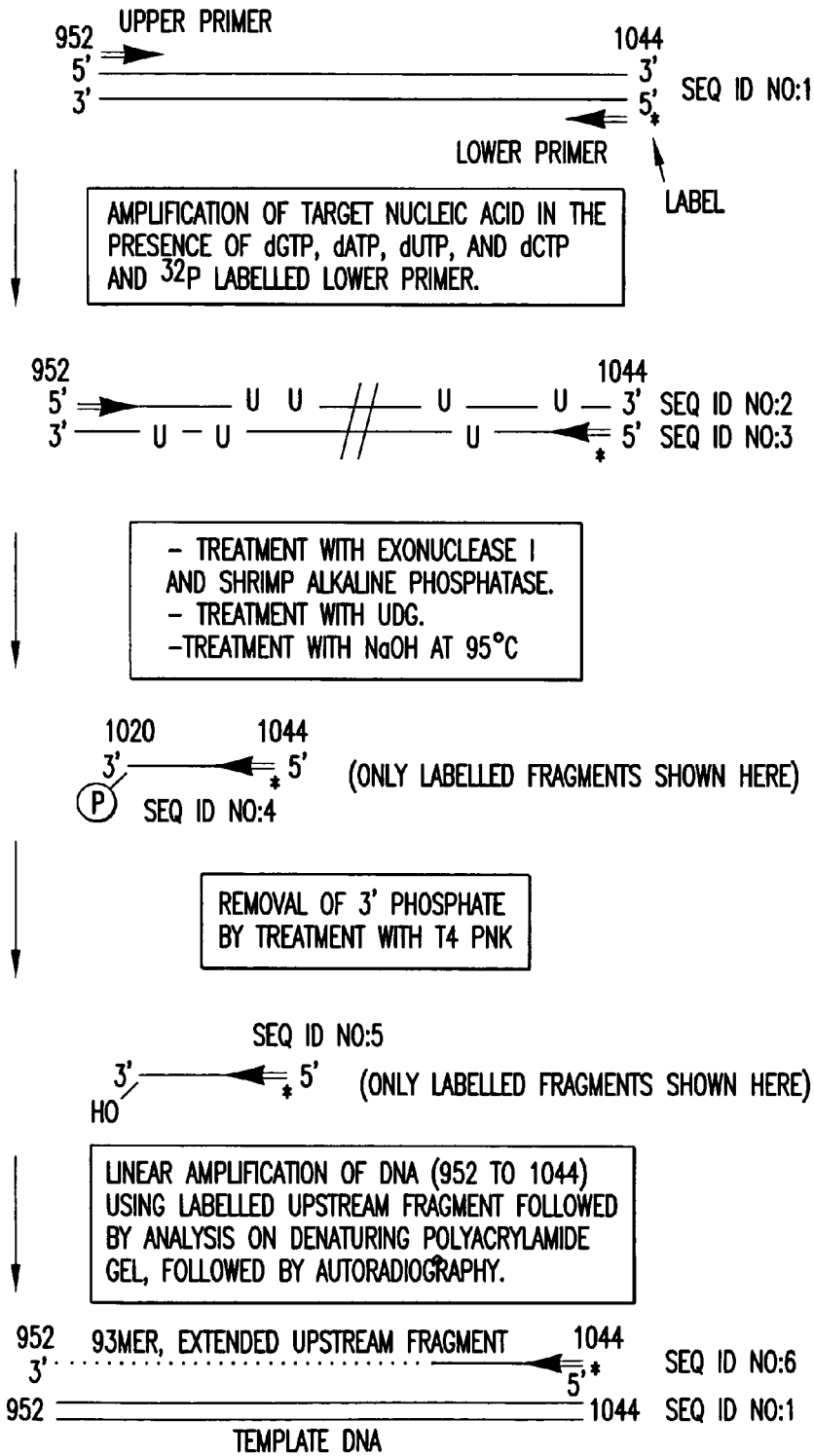
FIG. 2 is a schematic representation of the method according to the invention as described in Example 1.

FIG. 2 is a schematic diagram of the target nucleic acid and the upper and lower primers (primers contain standard bases, G, A, T and C). Six pmoles of the lower primer was end labelled by incubation with 1 unit of T4 Polynucleotide Kinase (commercially available from New England Biolabs), 70 mM Tris-HCl (pH7.6), 10 mM $MgCl_2$, 5 mM dithiothreitol and 1 µCi $\gamma^{32}P$ ATP (3000 Ci/mmol) for 30 min at 37° C. The target nucleic acid sample was amplified by PCR in a reaction mix containing target nucleic acid, 0.2 mM dATP, dCTP, dGTP and dUTP, 6 pmoles of $^{32}P$ labelled lower primer and non-labelled upper primer in a total volume of 19 µl. The reaction mix was then overlaid with an equal volume of mineral oil and a hot start PCR was performed whereby the reaction mix was heated to 94° C. for 5 min prior to addition of 1 unit of Taq polymerase (available from Promega) (bringing the total volume to 20 µl). 30 cycles of denaturation, annealing and extension were carried out in a thermocycler. The reaction mixture bearing the amplified target nucleic acid was then treated with exonuclease I (available from Amersham Life Sciences) to digest the primers not extended in the amplification step and shrimp alkaline phosphatase (SAP) (available from Boehringer Mannheim) to digest the dNTPs not incorporated during the amplification step. This was achieved by incubating 10 µl of the PCR reaction with 0.5 units of exonuclease I and 1 unit of SAP at 37° C. for 30 min. Exo I and SAP were subsequently heat inactivated by incubating the reaction at 80° C. for 15 min.

Uracil DNA-glycosylase (available from New England Biolabs) (0.5 units) was then added and the incubation continued at 37° C. for 30 min. Following treatment with uracil DNA-glycosylase, the abasic sites generated in the amplified product were cleaved to completion by adding NaOH to a final concentration of 0.05M and heating the mixture for 15 min at 95° C. The digested DNA was then precipitated by adding 10% volume 3M sodium acetate and 2 volumes of ethanol. The pellet was resuspended in 5 µl water. The digested DNA was then treated with 0.5 units of T4 polynucleotide kinase (PNK) which removes the phosphate group from the 3' terminii.

A linear amplification reaction was then carried out using the products of the above cleavage reaction, the fragment of interest being the labelled upstream extendible fragment, during which, the upstream extendible fragment is extended by a thermostable DNA polymerase in a cycling reaction in a total volume of 10 µl. The template for this reaction is amplified target nucleic acid (952 to 1044 of RYR1 gene) which is free from primers due to pretreatment with ExoI.

An equal volume of formamide loading dye (90% formamide, 0.025% bromophenol blue, 0.025% xylene cylanol) was added to the sample which was then heated at 85° C. for 5 min. The sample was then loaded onto a 20% denaturing (7M urea) polyacrylamide gel and electrophoresis was carried out for 3–4 hours at 60 W for size analysis of the extension products. Following electrophoresis, autoradiography was carried out by exposing the gel directly to X-ray photographic film for 12 hrs at −70° C.

Analysis of the autoradiograph, where the lower primer was labelled, showed a product of 93 nucleotides in length. This product was not observed if the T4 polynucleotide kinase treatment or the linear amplification reaction was not included in the above procedure.

Example 2

The method according to the invention was used to detect the presence of a G to A mutation at position 1021 in the human RYR1 gene. cDNA from a normal individual and from an individual affected with Malignant Hyperthermia was amplified by using upper (952 to 972) and lower (1204 to 1224) primers to generate a 273 bp double stranded DNA fragment (952 to 1224)(As in the case of Example 1 nucleotide numbers refer to the sequence of the RYR1 gene).

FIGS. 3 and 4 are schematic diagrams of the target nucleic acid and the upper and lower primers (primers contain standard bases, G, A, T and C). The target nucleic acid sample was amplified by PCR in a reaction mix containing target nucleic acid, 0.2 mM dATP, dCTP, dGTP and 0.19 mM dTTP and 0.01 mM dUTP, and 6 pmoles of upper and lower primers in a total volume of 19 µl. The reaction mix was then overlaid with an equal volume of mineral oil and a hot start PCR was performed whereby the reaction mix was heated to 94° C. for 5 min prior to addition of 1 unit of Taq polymerase (bringing the total volume to 20 µl). 30 cycles of denaturation, annealing and extension were carried out in a thermocycler. The reaction mixture bearing the amplified target nucleic acid was then treated with exonuclease I to digest the primers not extended in the amplification step and shrimp alkaline phosphatase (SAP) to digest the dNTPs not incorporated during the amplification step. This was achieved by incubating 10 µl of the PCR reaction with 0.5 units of exonuclease I and 1 unit of SAP at 37° C. for 30 min. Exo I and SAP were subsequently heat inactivated by incubating the reaction at 80° C. for 15 min.

Uracil DNA-glycosylase (0.5 units) was then added and the incubation continued at 37° C. for 30 min. Following treatment with uracil DNA-glycosylase, the abasic sites generated in the amplified product-were cleaved to completion by adding NaOH to a final concentration of 0.05M and heating the mixture for 15 min at 95° C. The digested DNA was then precipitated by adding 10% volume 3M sodium acetate and 2 volumes of ethanol. The pellet was resuspended in 5 µl water. The digested DNA was then treated with 0.5 units of T4 Polynucleotide Kinase which removes the phosphate group from the 3' terminii.

A linear amplification reaction was then carried out using the products of the above cleavage reaction, i.e. the various extendible upstream fragments, during which, the upstream fragment is extended by a thermostable DNA polymerase (i.e. Thermosequenase (available from Amersham Life Sciences)) in a cycling reaction in a total volume of 10 μl. The template for this reaction is amplified fragment of normal cDNA (952 to 1224 of RYR1 gene) which is free from unlabelled primers due to pretreatment with ExoI. The extension reaction is carried out in the presence of 1 mM of three of the dideoxy terminator nucleotides (ddNTP) and 0.02 mM of a $^{33}$P-labelled ddNTP.

An equal volume of formamide loading dye (90% formamide, 0.025% bromophenol blue, 0.025% xylene cylanol) was added to the sample which was then heated at 85° C. for 5 min. The sample was then loaded onto a 6% denaturing (7M urea) polyacrylamide gel and electrophoresis was carried out for 3–4 hours at 60 W for size analysis of the extension products. Following electrophoresis, autoradiography was carried out by exposing the gel directly to X-ray photographic film for 12 hrs at −70° C.

Analysis of the autoradiograph, where ddTTP was the labelled ddNTP (FIG. 3), showed a ladder of labelled fragments corresponding to the distance from the 5' end of the primers to the site of a dUMP incorporation (Only extension of the lower strand is shown). These sites corresponded to the wild type T pattern of the DNA. When mutant target nucleic acid was used to generate the extension primers, an additional band was observed in the T pattern of bands (203 nucleotides). Analysis of the autoradiograph, where ddCTP was labelled (FIG. 4) showed no labelled bands when amplified normal target nucleic acid was the source of upstream fragments, however, when amplified mutant target nucleic acid was used, analysis showed just one band. The size of the labelled fragment corresponds to the distance between the 5' end of the lower primer and the mutation site (i.e. 203 nucleotides) thereby demonstrating the presence of the G to A mutation at position 1021 of the RYR1 gene in that individual.

Example 3

The method according to the invention was used to detect the presence of a G to A mutation at position 6411 (codon 12) in the human Ki-ras gene. Genomic DNA from normal tissue and tumour tissue of an individual with colon cancer was amplified by using upper (6390 to 6409) and lower (6417 to 6443) primers to generate a 54 bp double stranded DNA fragment (6390 to 6443)(Nucleotide numbers refer to the genomic sequence of the Ki-ras gene including introns).

FIG. 5 is a schematic diagram of the target nucleic acid and the upper and lower primers (primers contain standard bases, G, A, T and C). The target nucleic acid sample was amplified by PCR in a reaction mix containing target nucleic acid, 0.2 mM dATP, dCTP, dGTP and dUTP and 6 pmoles of upper and lower primers in a total volume of 19 μl. The reaction mix was then overlaid with an equal volume of mineral oil and a hot start PCR was performed whereby the reaction mix was heated to 94° C. for 5 min prior to addition of 1 unit of Taq polymerase (bringing the total volume to 20 μl). 30 cycles of denaturation, annealing and extension were carried out in a thermocycler. The reaction mixture bearing the amplified target nucleic acid was then treated with Exonuclease I (Exo I) to digest the primers not extended in the amplification step and Shrimp Alkaline Phosphatase (SAP) to digest the dNTPs not incorporated during the amplification step. This was achieved by incubating 20 μl of the PCR reaction with 0.5 units of Exo I and 1 unit of SAP at 37° C. for 30 min. Exo I and SAP were subsequently heat inactivated by incubating the reaction at 80° C. for 15 min. Uracil DNA-glycosylase (0.5 units) and Endonuclease IV (1 unit) were then added and the incubation continued at 37° C. for 30 min to allow complete excision of all the uracils present in the amplified DNA and cleavage of the resulting abasic sites to completion.

This cleavage resulted in the upstream fragments having a 3' hydroxyl group at their 3' terminus which can be extended by action of a DNA polymerase.

Extension reactions were then carried out in a reaction mixture (10 μl) containing the products of the above cleavage reaction, i.e. the extendible upstream fragments (2 μl of cleavage reaction, approx. 1 pmol of extendible fragments), and 100 fmol of a synthetic template oligonucleotide, 0.2 mM dATP, dTTP, and dGTP, 0.02 mM dCTP, 1 μCi α$^{32}$PdCTP, 6 pmol reverse primer and 1 unit Taq DNA polymerase. The reaction was carried out for 40 cycles of denaturation, annealing and extension.

An equal volume of formamide loading dye (90% formamide, 0.025% Bromophenol blue, 0.025% Xylene cylanol) was added to the sample which was then heated at 85° C. for 5 min. The sample was then loaded onto a denaturing (7M urea) polyacrylamide gel and electrophoresis was carried out for 3–4 hours at 60 W for size analysis of the extension products. Following electrophoresis, autoradiography was carried out by exposing the gel directly to X-ray photographic film for 12 hrs at −20° C.

Analysis of DNA from normal tissue results in the generation of a 37 nucleotide extendible fragment following glycosylase mediated cleavage using the above mentioned upper and lower primers (FIG. 5). Similar analysis of DNA from tumour tissue results in the generation of a 32 nucleotide extendible fragment (FIG. 5). Analysis of the autoradiograph showed a 66 nucleotide band following analysis of DNA from normal tissue and using template oligonucleotide 1 (FIG. 6A). This band was not observed when template oligonucleotide 2 was used in the above analysis (FIG. 6B). Analysis of the autoradiograph showed a 66 nucleotide band following analysis of DNA from tumour tissue and using template oligonucleotide 2 (FIG. 6C). This band was not observed when template oligonucleotide 1 was used in the above analysis (FIG. 6D). Therefore the presence of a mutation at codon 12 of the Ki-ras gene was determined by the ability of the upstream fragment to be extended on a mutant template oligonucleotide whereas the upstream fragment was not extended on a normal template oligonucleotide and vice versa for the absence of the mutation.

Example 4

Example 3 was repeated to the stage where the abasic sites had been cleaved to completion. This cleavage resulted in the upstream fragments having a 3' hydroxyl group at their 3' terminus as before.

Figure 7:
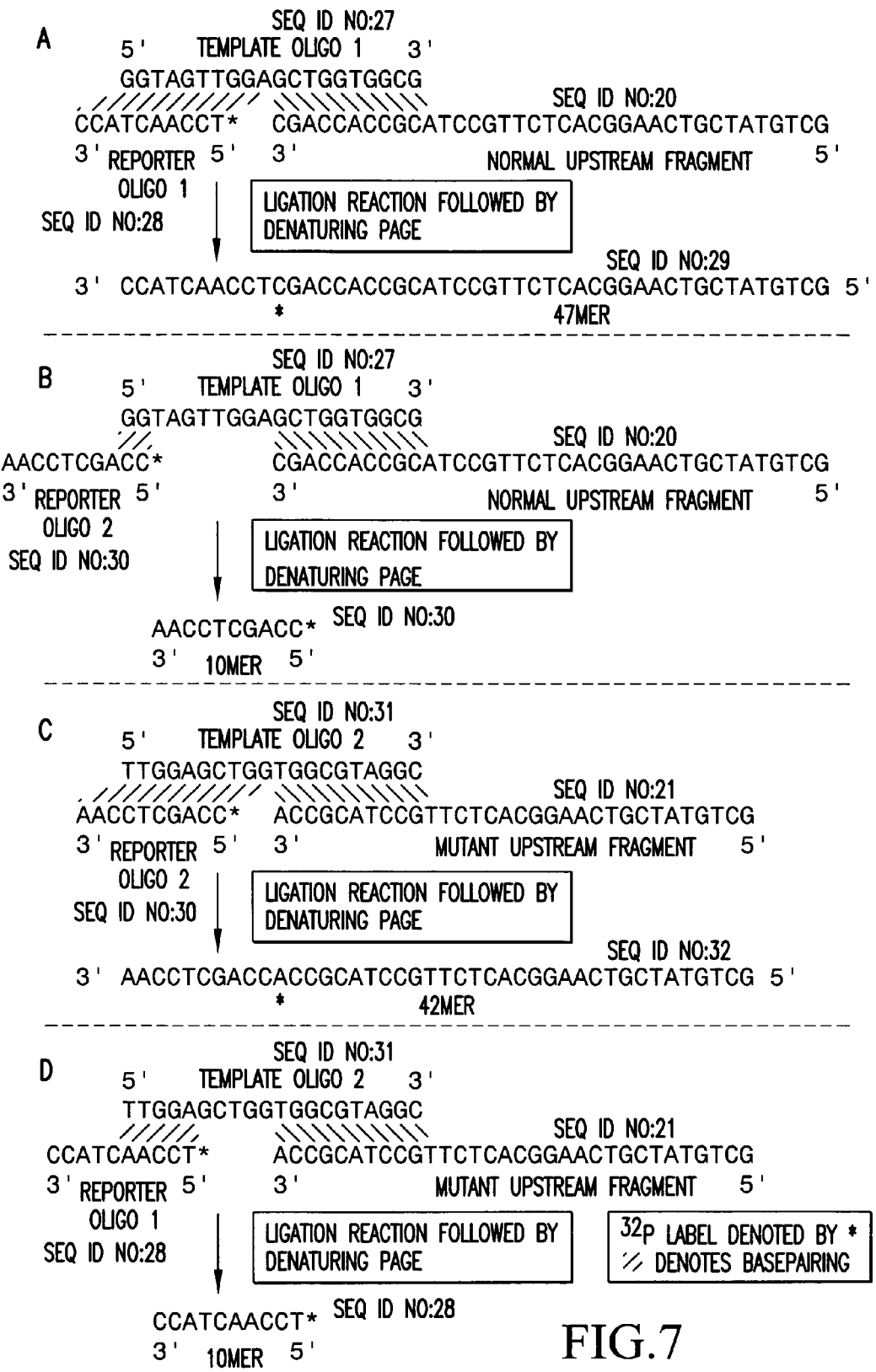
FIGS. 7A–7D is a schematic representation of the ligation reactions carried out in Example 4 on the upstream fragments and the products thereby obtained.

Reporter oligonucleotides 1 and 2 (FIG. 7)(complementary to nucleotides 6397 to 6406 (5' TCCAACTACC3' No. 1 (SEQ ID NO. 28)) and nucleotides 6402 to 6411 (5'CCAGCTCCAA3', No. 2 (SEQ ID NO. 30)) of the Ki-ras gene respectively) were 5' endlabelled using γ$^{32}$PATP and T4 polynucleotide kinase. This served to label the resulting ligated fragment and also provided a 5' terminus phosphate on the reporter oligonucleotide which is required for any possible ligation.

Ligation reactions (16° C. for 60 min) were then carried out using the products of the above cleavage reaction, i.e. the extendible upstream fragments (5 μl of cleavage reaction, approx. 2 pmol of extendible fragments), 4 pmol of labelled reporter oligonucleotide and 2 pmol of a template oligonucleotide 1 or 2 (5'GGTAGTTGGAGCTGGTGGCG3' (SEQ ID No. 27) (nuc 6397 to 6416) or 5'TTGGAGCTG-GTGGCGTA GGC3' (SEQ ID No. 31) (nuc 6402 to 6421) respectively) (FIG. 7) and 1 unit T4 DNA ligase, during which, the upstream fragment is extended in length by the ligation of a reporter oligonucleotide in a 20 μl reaction.

An equal volume of formamide loading dye (90% formamide, 0.025% Bromophenol blue, 0.025% Xylene cylanol) was added to the sample which was then heated at 85° C. for 5 min. The sample was then loaded onto a denaturing (7M urea) polyacrylamide gel and electrophoresis was carried out for 3–4 hours at 60 W for size analysis of the extension products. Following electrophoresis, autoradiography was carried out by exposing the gel directly to X-ray photographic film for 3 hrs at −20° C.

Analysis of DNA from normal tissue results in the generation of a 37 nucleotide extendible fragment following glycosylase mediated cleavage using the above mentioned upper and lower primers (FIG. 5). Similar analysis of DNA from tumour tissue results in the generation of a 32 nucleotide extendible fragment (FIG. 5). Analysis of the autoradiograph showed a 47 nucleotide band following analysis of DNA from normal tissue and using reporter oligonucleotide 1 and template oligonucleotide 1 (FIG. 7A). This band was not observed when reporter oligonucleotide 2 was used in the above analysis (FIG. 7B). Analysis of the autoradiograph showed a 42 nucleotide band following analysis of DNA from tumour tissue and using reporter oligonucleotide 2 and template oligonucleotide 2 (FIG. 7C). This band was not observed when reporter oligonucleotide 1 was used in the above analysis (FIG. 7D). Therefore the presence of a mutation at codon 12 of the Ki-ras gene was determined by the presence of a 42 nucleotide band whereas the presence of the normal allele was determined by the presence of a 47 nucleotide band. Samples containing normal and tumour DNA yielded both 42 and 47 nucleotide bands.

The above analysis was also carried out where the lower primer was 5' endlabelled with $^{32}P$. This required that the reporter oligonucleotides be phosphorylated using unlabelled ATP as phosphate donor. The results were similar to those observed above in that a 42n band demonstrated the presence of the mutant Ki-ras gene (codon 12) whereas a 47n band demonstrated the absence of the mutation at codon 12 of the Ki-ras gene. In addition the above analysis was also carried out using the initially amplified Ki-ras gene fragment from normal or mutant sample as template during the ligation reaction. Normal amplified product was used instead of template oligonucleotide 1, whereas mutant amplified product was used instead of template oligonucleotide 2. Again the same results were observed as described above.

As indicated above, the method according to the invention has numerous advantages over known methods, especially the method of WO 97/03210. After the glycosylase mediated cleavage in the case of WO 97/03210 (which can be carried out in a number of ways and which yields a number of different 3' termini), the resulting DNA fragments are not further processed and are analysed directly. In the present invention, the glycosylase mediated cleavage step is followed by a step that permits extension of the 3' termini generated by glycosylase mediated cleavage.

A major advantage of the present invention, which is not possible in the case of the prior art methods, is that the present invention allows detection of sequence differences such as mutations and polymorphisms between nucleic acid molecules without detecting sequence similarities. As indicated above, it is not possible with the method of WO 97/03210 to detect sequence differences between nucleic acid molecules without detecting sequence similarities. This is a limitation of the method of WO 97/03210 as multiple samples cannot be combined for simultaneous analysis. The present invention also allows for the analysis of multiple genes or gene segments simultaneous analysis. Furthermore, the present invention allows for the generation of specific primers for amplification of nucleic acids without the necessity of having prior knowledge of the sequence of the nucleic acid. This is not possible with the known methods. In addition, the present invention permits the generation of specific primers from nucleic acids in a unique way and such primers can be subsequently assayed by polymerase extension to determine the nature of the sequence at the 3' termini of said primers.

The invention claimed is:

1. A method for characterising nucleic acid molecules, which comprises the steps of:
   i) introducing a modified base which is a substrate for a DNA glycosylase into a DNA molecule by enzymatic extension of the molecule on a template nucleic acid;
   ii) excising the modified base by means of said DNA glycosylase so as to generate an abasic site;
   iii) cleaving the DNA at the abasic site so as to generate and release an extendible upstream DNA fragment having a 3' hydroxyl terminus, wherein the sequence of the extendible fragment is determined by the sequence of the template nucleic acid; and
   iv) incubating the released extendible upstream DNA fragment in the presence of an enzyme allowing for extension thereof and a selected template nucleic acid, which has partial or full sequence complementarity to said upstream DNA fragment and analysing resultant fragment(s) to detect the presence or absence of a mutation.

2. A method according to claim 1, wherein the upstream fragment is generated by cleaving the DNA at the 5'side of the abasic site, such that the 3'terminus of the upstream fragment bears a hydroxyl group.

3. A method according to claim 2, wherein the cleavage is achieved with a 5'AP endonuclease.

4. A method according to claim 1, wherein the upstream fragment is generated by cleaving at the 5' side of the abasic site so as to leave a phosphate group at the 3'terminus of the upstream fragment and removing the phosphate group so that the upstream fragment bears a hydroxyl group at the 3'terminus.

5. A method according to claim 1, wherein the upstream fragment is generated by cleaving at the 3'side of the abasic site so as to generate a deoxyribose phosphate group at the 3'terminus of the upstream fragment and subsequently removing the deoxyribose group to leave a hydroxyl group at the 3'terminus.

6. A method according to claim 1, wherein 5' deoxyribose moieties downstream of the 3'terminus of the upstream fragment are removed so that the upstream fragment can be extended on the template.

7. A method according to claim 6, wherein the 5'deoxyribose moieties are removed by a 5'deoxyribophosphodiesterase.

8. A method according to claim 1, wherein the modified base is introduced by enzymatic amplification of the DNA.

9. A method according to claim 8, wherein the amplified strands are separated for a separate analysis of the respective strands.

10. A method according to claim 8, wherein a primer or one or more nucleotide (s) involved in the enzymatic amplification is labelled.

11. A method according to claim 1, wherein the enzyme is a polymerase.

12. A method according to claim 11, wherein the extendible upstream fragment is incubated in step iv) with the polymerase in the presence of one or more nucleotide (s).

13. A method according to claim 12, wherein one or more of the nucloeotide (s) of step iv) is a dideoxy nucleotide.

14. A method according to claim 12, wherein one or more of the nucleotide (s) of step iv) is labelled.

15. A method according to claim 11, wherein the extension of step iv) is achieved by means of an amplification reaction using said extendible DNA fragment.

16. A method according to claim 11, wherein the extension of step iv) is achieved by means of an amplification reaction including a primer in addition to using said extendible DNA fragment.

17. A method according to claim 1, wherein the enzyme is a ligase.

18. A method according to claim 17, wherein the extendible upstream fragment is incubated with the ligase in the presence of a reporter oligonucleotide.

19. A method according to claim 18, wherein the reporter oligonucleotide is partially degenerate.

20. A method according to claim 1, wherein any extended fragments resulting from step iv) are detected by hybridisation.

21. A method according to claim 1, which is used to detect a known or unknown mutation.

22. A method according to claim 1, wherein the method is used to analyse the CpG content of DNA by detecting C to T transitions in DNA.

* * * * *